US012329952B1

(12) United States Patent
Denyer et al.

(10) Patent No.: US 12,329,952 B1
(45) Date of Patent: Jun. 17, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB); Thomas Lever, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,040

(22) Filed: Aug. 29, 2024

(51) Int. Cl.
*A61M 5/32* (2006.01)

(52) U.S. Cl.
CPC .............................. *A61M 5/3204* (2013.01)

(58) Field of Classification Search
CPC .... A61M 5/3204; A61M 5/32; A61M 5/3202; A61M 5/321; A61M 5/3271; A61M 5/3272; A61M 5/326; A61M 5/3257; A61M 2005/3268; A61M 2005/3261
See application file for complete search history.

(56) References Cited

U.S. PATENT DOCUMENTS

| | | | |
|---|---|---|---|
| 4,118,611 | A | 10/1978 | Harris |
| 4,994,045 | A | 2/1991 | Ranford |
| 6,547,764 | B2 | 4/2003 | Larsen et al. |
| 8,858,510 | B2 | 10/2014 | Karlsson |
| 9,919,107 | B2 | 3/2018 | Imai et al. |
| 2002/0133122 | A1 * | 9/2002 | Giambattista ......... A61M 5/326 604/198 |
| 2007/0078408 | A1 | 4/2007 | Wang |
| 2012/0041368 | A1 | 2/2012 | Karlsson |

FOREIGN PATENT DOCUMENTS

WO    WO-2022117682 A1 *  6/2022  .......... A61M 5/3245

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.
Speciale et al., "Snap-Through Buckling Mechanism for Frequency-up Conversion in Piezoelectric Energy Harvesting," Applied Sciences, May 23, 2020, 10(10):3614, 18 pages.
U.S. Appl. No. 18/819,222, filed Aug. 29, 2024, Timothy Denyer.
U.S. Appl. No. 18/819,371, filed Aug. 29, 2024, Timothy Denyer.

* cited by examiner

*Primary Examiner* — Bhisma Mehta
*Assistant Examiner* — Hamza A Darb
(74) *Attorney, Agent, or Firm* — Fish & Richardson P.C.

(57) ABSTRACT

A medicament delivery device has a needle for injecting medicament, a body and a needle cover. The needle cover is axially movable relative to a locked position in which the needle cover covers the distal end of the needle. The device has an inner housing with an aperture. A collar is located at least partially within the inner housing and is configured to rotate relative to the inner housing. The collar has one or more arms. A rotational member rotates the collar from a first position to a second position. When the needle cover is in the locked position and the collar is in the second position then the arm extends radially through the aperture and blocks proximal movement of the needle cover away from the locked position.

25 Claims, 5 Drawing Sheets

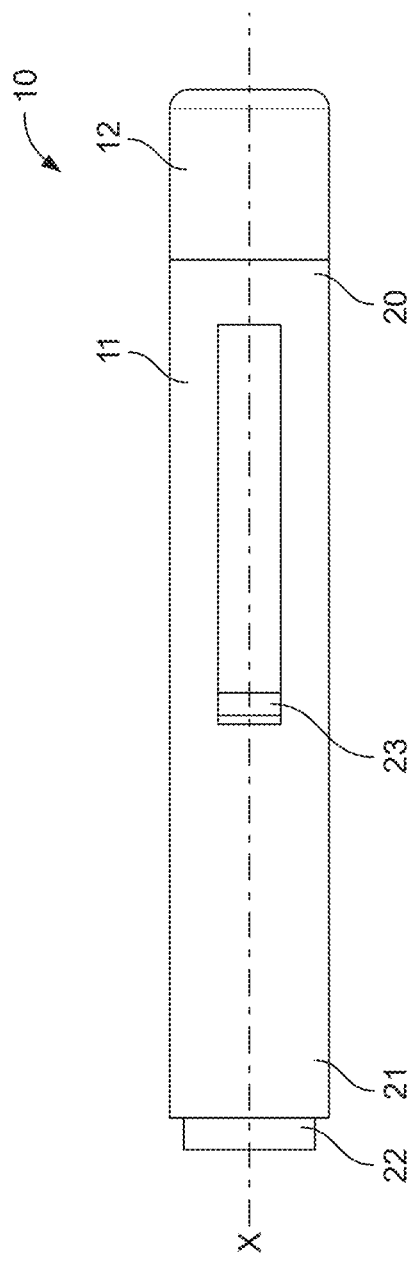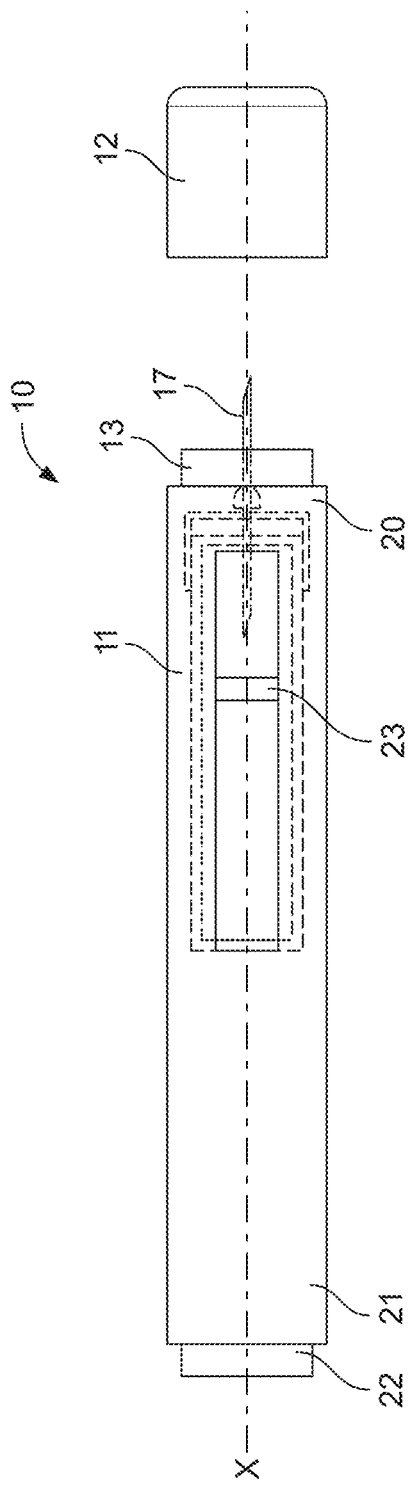
FIG. 1A
FIG. 1B

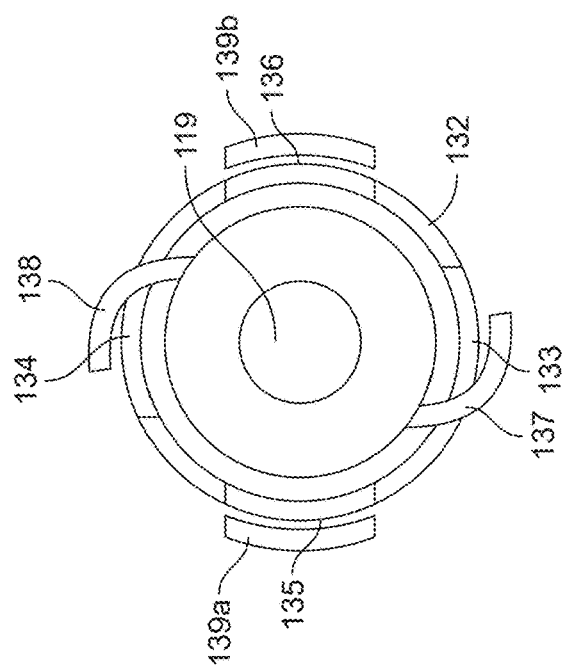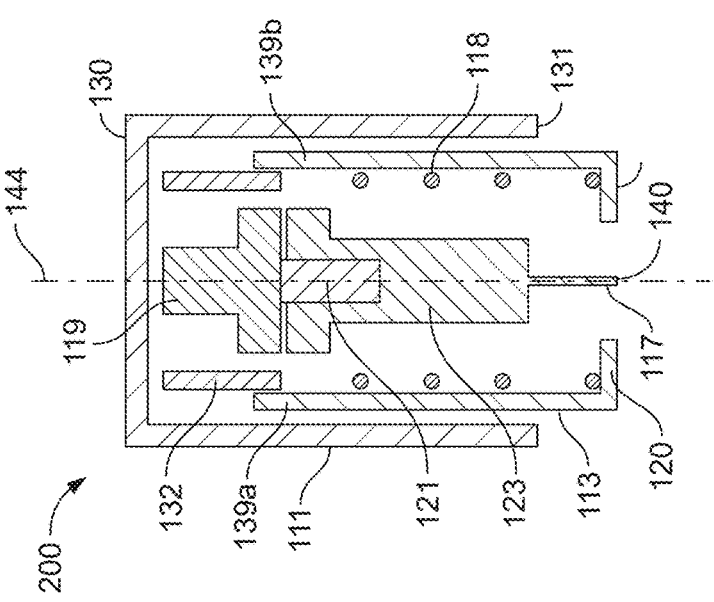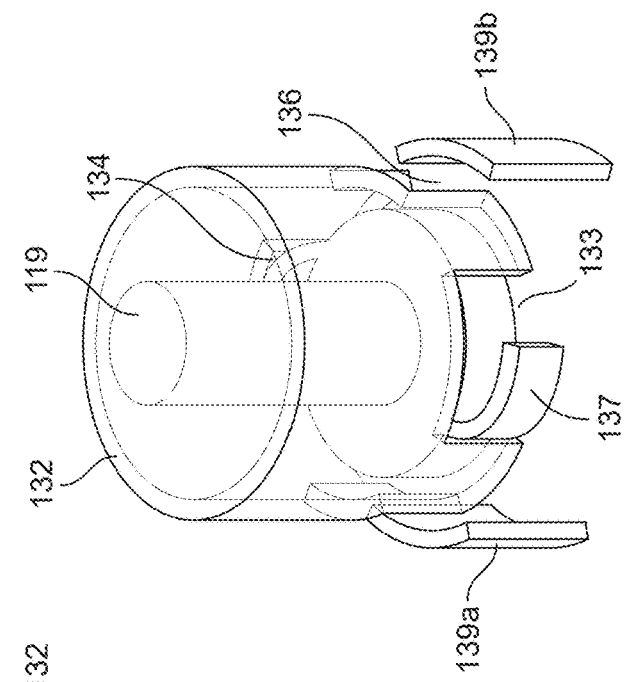

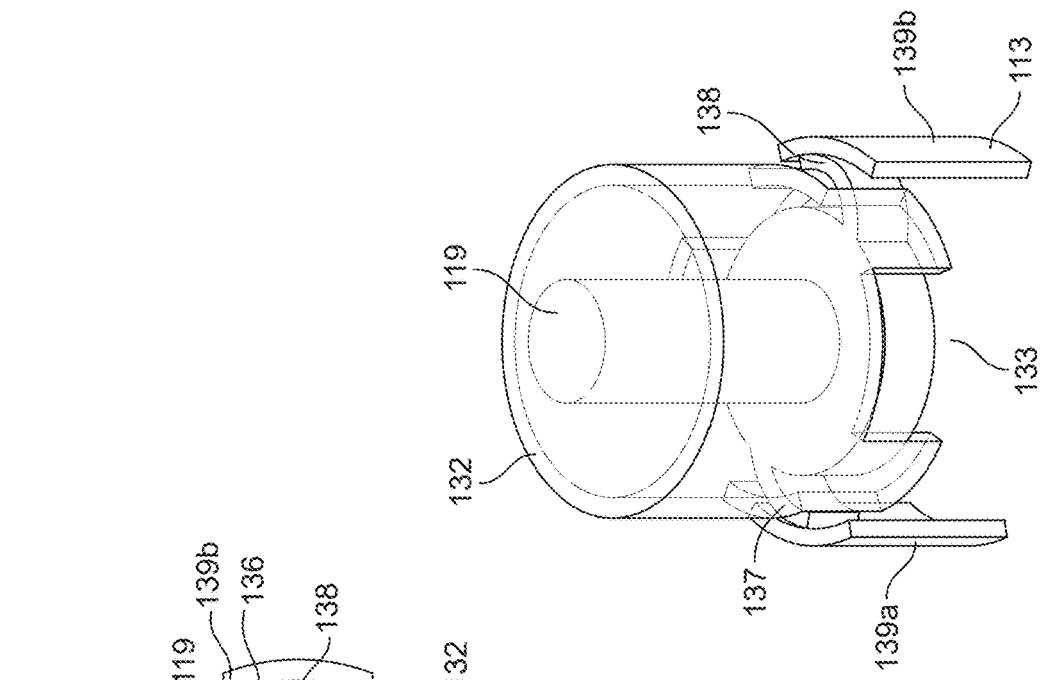
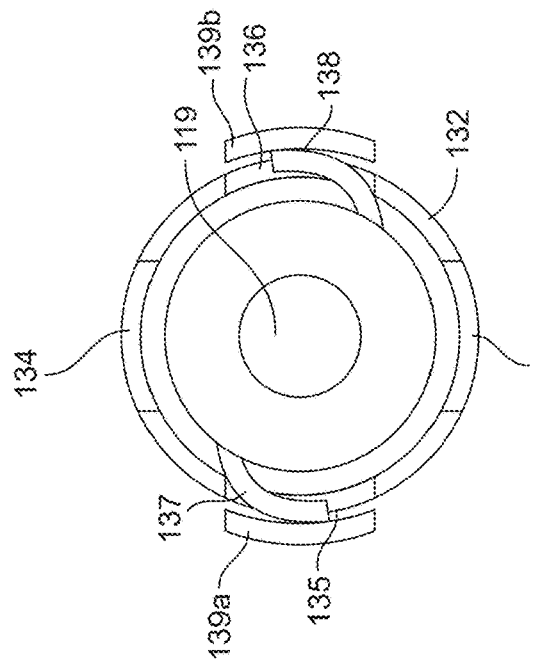
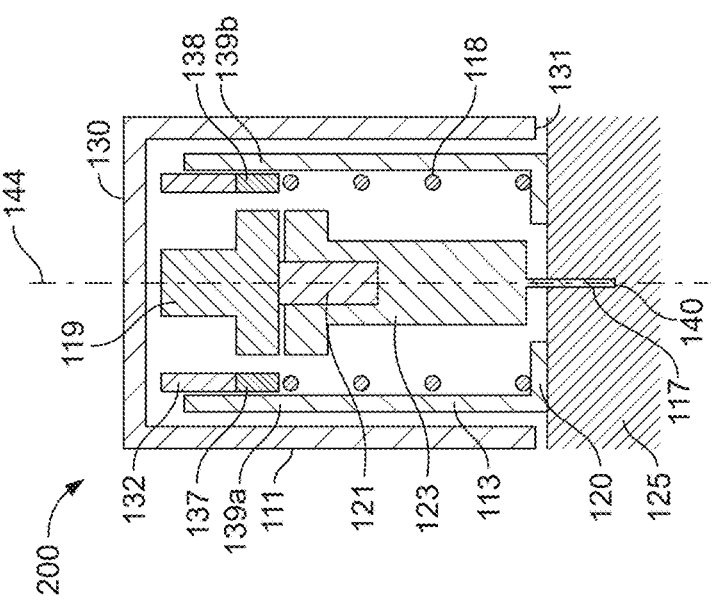

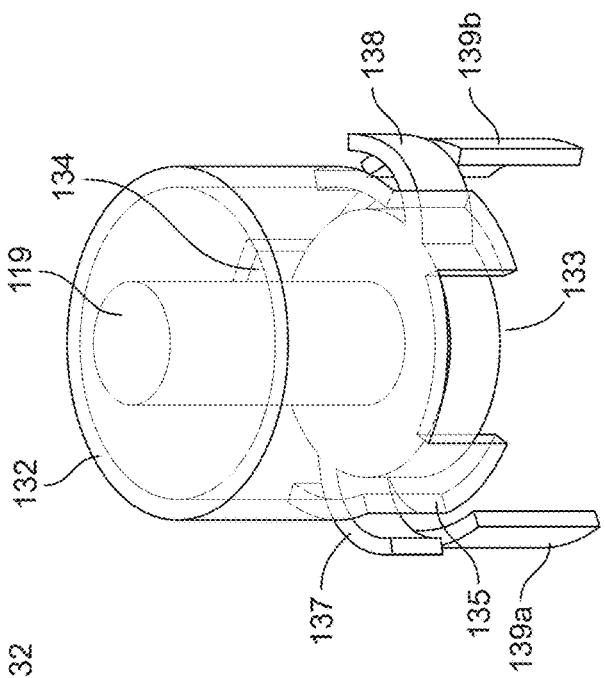
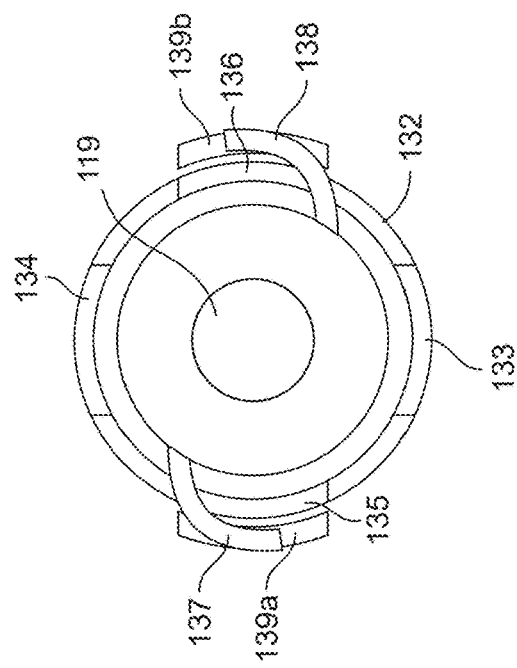
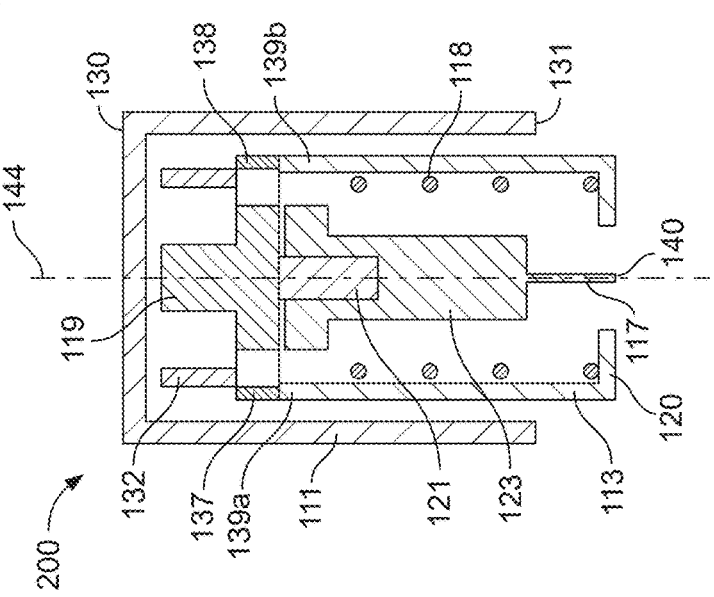
FIG. 5C
FIG. 5B
FIG. 5A

MEDICAMENT DELIVERY DEVICE

TECHNICAL FIELD

This application relates to a medicament delivery device and a method of using a medicament delivery device.

BACKGROUND

Medicament delivery devices are used to deliver a range of medicaments.

In some devices, the device must be held in a holding position at an injection site, to ensure that the correct dose of medicament is dispensed from the device, before removing the device from the injection site.

It may be difficult to hold the device in the holding position whilst the medicament is dispensed. This may result in pain, discomfort, a wet injection site, early device removal and/or partial delivery of the medicament.

It is an object of the present disclosure to provide an improved medicament delivery device.

SUMMARY

According to a first aspect of the present disclosure, there is provided a medicament delivery device comprising a needle for injecting medicament; a body having a proximal end and a distal end; a needle cover, wherein the needle cover is axially movable relative to the body from a holding position in which the needle protrudes from the distal end of the needle cover for injecting medicament, to a locked position in which the needle cover covers the distal end of the needle; a biasing member configured to bias the needle cover axially in the distal direction; an inner housing comprising an aperture; a collar located at least partially within the inner housing and configured to rotate relative to the inner housing, wherein the collar comprises an arm; and a rotational member for rotating the collar from a first position to a second position, wherein the needle cover is arranged radially outwardly from the inner housing, and wherein when the needle cover is in the locked position and the collar is in the second position then the arm extends radially through the aperture to a blocking position and blocks proximal movement of the needle cover away from the locked position.

The needle cover may at least partially covers the aperture when the needle cover is in the holding position for restricting radial movement of the arm through the aperture. The arm may be positioned within the aperture when the needle cover is in the holding position and the collar is in the second position.

The needle cover may be axially movable relative to the body from an initial position, in which the needle cover covers the distal end of the needle, to the holding position. The arm may not be located in the aperture when the collar is in the first position and the needle cover is in the initial position.

The aperture may be a first aperture, and the inner housing may comprise a second aperture for receiving the arm.

The arm may extend through the second aperture when the needle cover is in the initial position and the collar is in the first position.

The arm may be a first arm, and the collar may further comprise a second arm.

The inner housing may comprise a further aperture for receiving the second arm, and wherein when the needle cover is in the locked position and the collar is in the second position then the second arm extends radially through the further aperture to a second blocking position and blocks proximal movement of the needle cover away from the locked position.

The needle cover may at least partially cover the further aperture when the needle cover is in the holding position for restricting radial movement of the second arm through the further aperture. The second arm may be positioned within the further aperture when the needle cover is in the holding position and the collar is in the second position.

The inner housing may comprise an additional aperture, and wherein the second arm extends through the additional aperture when the needle cover is in the initial position and the collar is in the first position.

The arm may be radially biased towards the blocking position. The arm may be flexible. The device may further comprise a spring which biases the arm radially outwards.

The inner housing may support the rotational member. The rotational member may be a spring. The rotational member may be a torsion spring.

Rotation of the collar from the first position to the second position may cause medicament to be dispensed from the device via the needle.

The medicament delivery device may be configured to inject greater than 2 ml of medicament. The medicament delivery device may be configured to inject medicament having a viscosity of greater than 25 cP.

The device may comprise the medicament.

According to another aspect of the present disclosure there is provided a method of locking a medicament delivery device after medicament has been dispensed from the medicament delivery device, the method comprising moving a needle cover of the device to a locked position in which the needle cover covers the distal end of a needle of the device, wherein when the needle cover is in the locked position then proximal movement of the needle cover away from the locked position is blocked by an arm.

The medicament delivery device may have any of the features as described and/or contemplated herein.

According to another aspect of the present disclosure there is provided a method of using a medicament delivery device, the method comprising removing the medicament delivery device from an injection site, wherein removing the medicament delivery device from the injection site moves a needle cover of the device to a locked position in which the needle cover covers the distal end of the needle, wherein when the needle cover is in the locked position then proximal movement of the needle cover away from the locked position is blocked by an arm.

The method may further comprise the preceding step of pressing the medicament delivery device against the injection site to move the needle cover from an initial position to a holding position for dispensing medicament from the device.

The method may further comprise holding the medicament delivery device in the holding position whilst medicament is dispensed from the device. The medicament delivery device may further comprise a a body having a proximal end and a distal end.

The needle cover may be axially movable relative to the body from a holding position in which the needle protrudes from the distal end of the needle cover for injecting medicament, to a locked position in which the needle cover covers the distal end of the needle.

The medicament delivery device may further comprise a biasing member configured to bias the needle cover axially in the distal direction. The medicament delivery device may further comprise an inner housing comprising an aperture.

The medicament delivery device may further comprise a collar located at least partially within the inner housing and configured to rotate relative to the inner housing. The collar may comprise the arm.

The medicament delivery device may further comprise a rotational member for rotating the collar from a first position to a second position. The needle cover may be arranged radially outwardly from the inner housing. When the needle cover is in the locked position and the collar is in the second position then the arm may extend radially through the aperture to a blocking position to block proximal movement of the needle cover away from the locked position.

The rotation of the collar from the first position to the second position may cause medicament to be dispensed from the device via the needle.

The movement of the needle cover from the initial position to the holding position may cause medicament to be dispensed from the device via the needle.

The device may comprise a mechanism configured to dispense medicament from the device via the needle when the needle cover reaches a predetermined axial position. Movement of the needle cover from the initial position to the holding position may trigger the mechanism to dispense medicament from the device via the needle.

The medicament delivery device may comprise a container for containing the medicament. The medicament may be located in the container. The container may be a syringe. The syringe may comprise the needle. The container may be a cartridge which is initially separated from the needle when the needle cover is in the initial position.

BRIEF DESCRIPTION OF THE FIGURES

Embodiments will now be described, by way of example only, with reference to the accompanying drawings, in which:

FIG. 1A shows an injector device with a cap attached;

FIG. 1B shows the injector device of FIG. 1A with the cap removed;

FIG. 3A shows a simplified view of an example medicament delivery device when the needle cover is in the initial position;

FIG. 3B shows a top view of part of the device of FIG. 3A when the needle cover is in the initial position;

FIG. 3C shows a perspective view of part the device of FIG. 3A when the needle cover is in the initial position;

FIG. 4A shows a simplified view of the device of FIG. 3A when the needle cover is in the holding position;

FIG. 4B shows a top view of part of the device of FIG. 3A when the needle cover is in the holding position;

FIG. 4C shows a perspective view of part the device of FIG. 3A when the needle cover is in the holding position;

FIG. 5A shows a simplified view of the device of FIG. 3A when the needle cover is in the locked position;

FIG. 5B shows a top view of part of the device of FIG. 3A when the needle cover is in the locked position; and FIG. 5C shows a perspective view of part the device of FIG. 3A when the needle cover is in the locked position.

DETAILED DESCRIPTION

Figure 2:
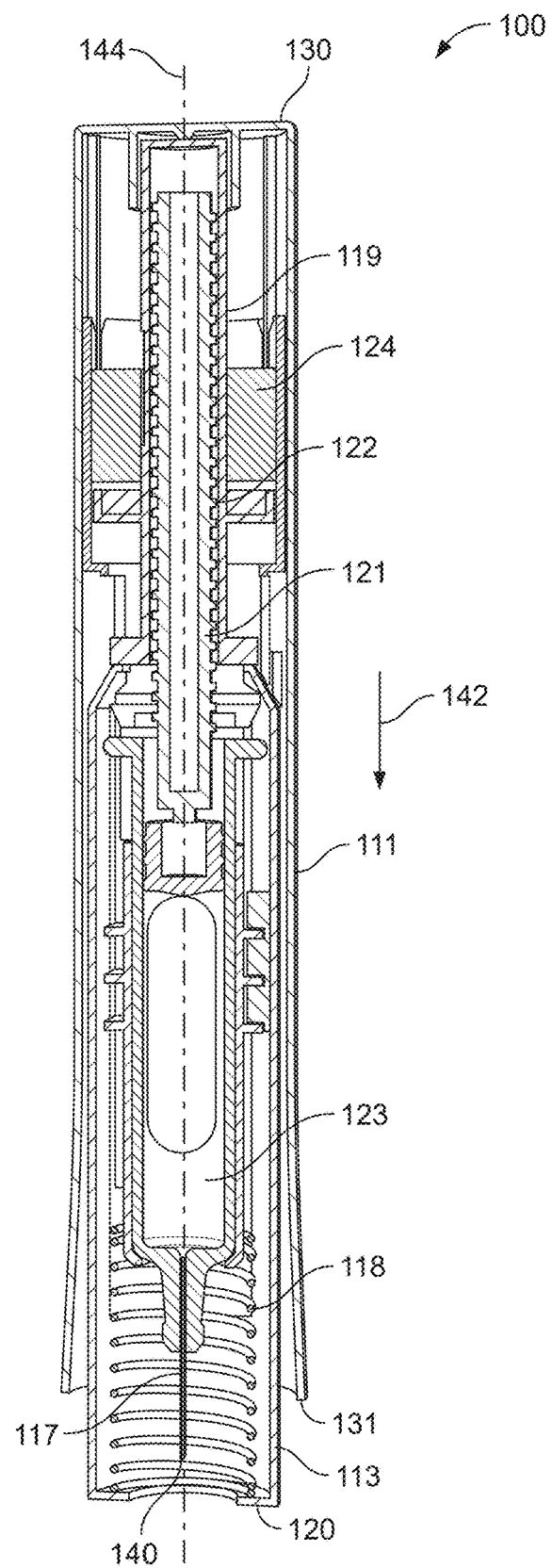
FIG. 2 shows a medicament delivery device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11. Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 shows a simplified view of a medicament delivery device 100. The medicament delivery device 100 has a needle 117 for injecting medicament, a body 111 having a proximal end 130 and a distal end 131, and a needle cover 113. The needle 117 has a distal end 140. The needle cover 113 is proximally movable relative to the body 111 between an initial position, in which the needle cover 113 covers the distal end 140 of the needle, and a holding position for dispensing medicament from the device. The device 100 extends along an axis 144.

The device 100 is shown in the initial position in FIG. 2. In the holding position the needle cover 113 is located proximally relative to the initial position. In the holding position the needle 117 protrudes from the distal end 120 of the needle cover 113.

The medicament delivery device further comprises a biasing member such as a spring 118 configured to bias the needle cover 113 axially in the distal direction. The distal direction is indicated by the direction of the arrow 142 in FIG. 2.

The medicament delivery device has a plunger 121 which is axially movable within a syringe 123 of the device to dispense medicament from the syringe 123 via the needle 117.

The medicament delivery device has a collar 119. The collar 119 is axially fixed relative to the body 111. The collar 119 interfaces with the plunger 121 via a screw thread 122. The medicament delivery device 100 has a rotational member such as a biasing member such as a spring 124, that is configured to rotate the collar 119 when the spring 124 is released. The spring 124 may be a torsion spring. The torsion spring 124 is released when the needle cover 113 reaches a predetermined axial displacement with a release mechanism (not shown). The rotation of the collar 119 causes the plunger 121 to move distally within the syringe 123, in view of the screw thread 122, to thereby dispense medicament from the syringe 123 via the needle 117.

The needle cover 113 is pressed against an injection site, thereby moving the needle cover 113 axially into the body 111 and uncovering the needle 117. The axial displacement of the needle cover 113 causes the release of the spring 124 which rotates the collar 119. The rotation of the collar 119 moves the plunger 121 axially within the syringe 123 to dispense the medicament via the needle 117.

The device 100 is pressed against the injection site 125, to hold the needle cover 113 at the holding position whilst the medicament is dispensed from the device.

After the medicament has been dispensed, the device 100 is removed from the injection site. The needle cover 113 moves distally under the force of the spring 118 to a locked position. In the locked position, the needle cover 113 covers the distal end 140 of the needle. In the locked position, the needle cover is prevented from moving proximally.

The medicament delivery device 100 is configured to inject greater than 2 ml of medicament and/or the medicament delivery device 100 is configured to inject medicament having a viscosity of greater than 25 cP.

FIGS. 3A to 3C show a simplified view of a medicament delivery device 200. The features described and/or contemplated in relation to the medicament delivery device 200 may be incorporated in the medicament delivery device 100 described and/or contemplated above.

The features described and/or contemplated in relation to the medicament delivery device 200 may be incorporated in another medicament delivery device, for example a medicament delivery device having a different mechanism for dispensing medicament to that described in relation to the medicament delivery device 100, and/or a medicament delivery device which is configured to inject 2 ml or less of medicament and/or a medicament delivery device which is configured to inject medicament having a viscosity of 25 cP or less, and/or a medicament delivery device in which the medicament is contained in a cartridge which is initially separated from the needle when the needle cover is in the initial position.

In FIGS. 3A to 3C, 4A to 4C and 5A to 5C, the reference numerals correspond to corresponding features described and/or contemplated above in relation to FIG. 2.

The medicament delivery device 200 has a needle 117 for injecting medicament, and a body 111 having a proximal end 130 and a distal end 131. The device 200 has a needle cover 113, wherein the needle cover 113 is axially movable relative to the body 111. The needle cover 113 is proximally movable from an initial position in which the needle cover 113 covers the distal end 140 of the needle 117 as shown, for example, in FIGS. 3A to 3C, to a holding position in which the needle 117 protrudes from the distal end 120 of the needle cover 113 for injecting medicament. An example of the holdings position is shown in FIGS. 4A to 4C, The needle cover 113 is distally movable from the holding position to a locked position in which the needle cover 113 covers the distal end 140 of the needle 117 as shown, for example, in FIGS. 5A to 5C.

The medicament delivery device 200 has a biasing member such as a spring 118 configured to bias the needle cover 113 axially in the distal direction. The needle cover 113 is movable from the initial position to the holding position against the biasing force of the spring 118.

A collar 119 is located at least partially within an inner housing 132. The collar 119 is configured to rotate relative to the inner housing 132 from a first position to a second position. The needle cover 113 is arranged radially outwardly from the inner housing 132. The inner housing 132 supports a rotational member which may be a second biasing member such as a spring 124. The spring 124 may be a torsion spring. In another embodiment, the inner housing 132 does not support the rotational member.

The collar 119 has a first arm 137. The collar 119 has a second arm 138. The first and second arms 137,138 could be seen to constitute a pair of arms. The first arm 137 is circumferentially separated from the second arm 138. For example, the first arm 137 is arranged 180° apart from the second arm 138. In another example, the first arm 137 could be arranged 90° apart or at other circumferential separations from the second arm 138.

The first arm 137 is flexible and is resiliently biased towards a first blocking position, which is discussed in further detail below. The second arm 138 is also flexible and is resiliently biased towards a second blocking position. In another embodiment the medicament delivery device additionally or alternatively comprises a first spring to bias the first arm 137 towards the blocking position and/or a second spring to bias the second arm 138 towards the second blocking position. The first and second blocking positions of the first and second arms 137, 138 are shown, for example, in FIGS. 5A to 5C.

In the first blocking position the first arm 137 extends through the first aperture 135. In the second blocking position the second arm 138 extends through the further aperture 136. When the needle cover is in the locked position and the collar is in the second position then the first arm 137 may be caused to extend through the first aperture 135 and the second arm 138 may be caused to extend through the further aperture 136 by other means, for example the first and second arms may not be biased towards the first and second blocking positions respectively.

In the illustrated example, two arms are provided but in another embodiment just one arm such as the first arm 137 could be provided, or more than two arms could be provided with each arm having corresponding features to those described herein.

The inner housing 132 has a first aperture 135, a second aperture 133, a further aperture 136 and an additional aperture 134.

When the needle cover is in the initial position then the collar 119 is in the first position. The first arm 137 extends radially through the second aperture 133 and the second arm 138 extends radially through the additional aperture 134.

The first arm 137 is not located in the first aperture 135 when the collar 119 is in the first position and the needle cover 113 is in the initial position. The second arm 138 is not located in the further aperture 136 when the collar 119 is in the first position and the needle cover 113 is in the initial position.

In another embodiment, the second and additional apertures 133, 134 are not present. In this embodiment, when the needle cover is in the initial position then the first and second arms 137, 138 may engage an inner surface of the inner housing 132. In another embodiment, when the needle cover is in the initial position and the collar 119 is in the first position then the first and second arms 137, 138 extend radially through the first aperture 135 and the further aperture 136, respectively.

If just one arm is present, then the inner housing may just have the first aperture 135 and optionally the second aperture 133.

As mentioned, the needle cover 113 is proximally movable from the initial position to the holding position as shown, for example, in FIGS. 4A to 4C.

To move the needle cover 113 to the holding position, the body 111 is held, for example by a user, and the needle cover 113 is pressed against an injection site 125 to move the needle cover 113 away from the initial position and axially into the body 111. When the needle cover 113 reaches a predetermined axial displacement within the body 111 then the spring 124 is released with a release mechanism. The spring 124 rotates the collar from the first position towards the second position when it is released.

The device 200 may be said to comprise a mechanism configured to dispense medicament from the device 200 via the needle 117 when the needle cover 113 reaches a predetermined axial position within the device. This mechanism may comprise the spring 124, the collar 119 and the piston 121, as described above in relation to the device 100, or it may be another mechanism. The rotation of the collar 119 from the first position to the second position may cause medicament to be dispensed from the device.

The medicament is dispensed from the device via the needle 117 whilst the needle cover 113 is in the holding position. The needle cover 113 is held in the holding position against the injection site 125, for example for a predetermined period of time, to ensure that the required dose of medicament is dispensed from the device 200. The needle cover 113 is held in the holding position against the force of the spring 118.

In another embodiment, the movement of the collar 119 from the first position to the second position does not cause medicament to be dispensed from the device 200 and another mechanism for dispensing the medicament from the device 200 may be provided.

When the needle cover 113 is in the holding position then the collar 119 is in the second position as shown, for example, in FIGS. 4A to 4C. The collar 119 has been rotated from the first position to the second position by the spring 124.

The collar 119 may reach the second position as soon as the needle cover 113 is in the holding position. In another embodiment, the collar 119 continuously rotates until the dose is complete and the collar 119 only reaches the second position once the drug delivery is complete or once the drug delivery is partially complete.

In another embodiment instead of providing a spring 124 such as a torsion spring to rotate the collar 119 form the first position to the second position, another rotational member may be provided such as a mechanical interface which causes the collar 119 to rotate when the needle cover is moved from the initial position to the holding position.

In the holding position, due to the rotation of the collar 119, the first arm 137 is positioned within the first aperture 135 and the second arm 138 is positioned within the further aperture 136.

The needle cover 113 at least partially covers the first aperture 135 and the further aperture 136 when the needle cover 113 is in the holding position and the collar 119 is in the second position for restricting radial movement of the first and second arms 137, 138 through the first and further apertures 135, 136 respectively. In another embodiment, the needle cover 113 fully covers the first aperture 135 and the further aperture 136 when the needle cover 113 is in the holding position and the collar 119 is in the second position for restricting radial movement of the first and second arms 137, 138 through the first and further apertures 138, 136 respectively.

The needle cover 113 is a sleeve with a first arm 139A extending proximally from the circular sleeve and a second arm 139B extending proximally from the sleeve. The first arm 139A contacts the first arm 137 when the needle cover 113 is in the holding position and the collar 119 is in the second position for restricting the outward radial movement of the first arm 137. The second arm 139B contacts the second arm 138 when the needle cover 113 is in the holding position and the collar 119 is in the second position for restricting the outward radial movement of the second arm 138.

In another embodiment the first arm 139A and the second arm 139B are not present. For example, the needle cover 113 could be in the form of a sleeve and the sleeve could contact the first and second arms 137, 138 when the needle cover 113 is in the holding position and the collar 119 is in the second position for restricting the outward radial movement of the first and second arms 137, 138.

After the medicament has been dispensed from the medicament delivery device 200, then the device 200 is removed from the injection site 125.

When the device 200 is removed from the injection site then the needle cover 113 moves distally from the holding position to the locked position under the force of the spring 118. The locked position is shown, for example, in FIGS. 5A to 5C. When the needle cover 113 is in the locked position then the collar 119 is in the second position. The distal movement of the needle cover 113 uncovers the first aperture 135 and the further aperture 136. The first arm 137 can then extend radially through the first aperture 135 to the first blocking position and the second arm 138 can extend radially through the further aperture 136 to the second blocking position.

When the first and second arms are in the first and second blocking positions respectively then they block proximal movement of the needle cover 113 away from the locked position. In the blocking position the first arm 137 extends radially outwardly of the inner housing 132. In the blocking position the second arm 138 extends radially outwardly of the inner housing 132. In other words, if the needle cover 113 tries to move proximally then it abuts the first and second arms 137, 138 which prevents proximal movement of the needle cover 113.

The needle 117 therefore cannot be exposed for stick injuries after the device 200 has been used.

If the medicament delivery device 200 did not have a locking functionality for preventing proximal movement of the needle cover 113 after use, then the spring 118 would need to be much stronger to ensure that the distal end 140 of the needle remains covered once the device has been used. Therefore, having the locking functionality in the device means that the spring 118 can be weaker, which consequently reduces the force that is required to be exerted to hold the device in the holding position.

In another embodiment, the needle cover 113 does not contact the first and second arms 137, 138 when the needle cover is in the holding position. For example, the first and second arms 137, 138 may be circumferentially offset from the first and further apertures 135, 136 when the needle cover is in the holding position. The collar 119 may only be rotated to its second position, when the first and second arms 137, 138 extend through the first and further apertures 135, 136 respectively, after the needle cover moves distally away from the holding position towards the locked position.

The medicament delivery device 200 may additionally have a cap which covers the distal end of the needle cover 113. The cap must be removed before the device 200 is used.

An example method of using the medicament delivery device will now be described.

The method involves removing the cap (if present) from the medicament delivery device 200. The method then involves pressing a needle cover 113 of the device against an injection site 125 to move the needle cover from an initial position to a holding position. The method then involves applying a holding force to the device to hold the needle cover 113 in the holding position against the injection site whilst medicament is dispensed from the device. The method then involves removing the device 200 from the injection site 125. The device is removed from the injection site 125 after the medicament has been dispensed from the device.

When the device 200 is removed from the injection site then the needle cover 113 is moved to a locked position in which the needle cover 113 covers the distal end 140 of the needle 117. The needle cover 113 is moved to the locked position under the force of the spring 118. When the needle cover 113 is in the locked position then proximal movement of the needle cover 113 away from the locked position is blocked by one or more arms 137, 138.

LIST OF FEATURES

10—Device
11—housing
12—cap
13—needle sleeve
17—needle
20—distal region
21—proximal region
22—button
23—piston
100—Device
111—body
113—needle cover
117—needle
118—spring
119—collar
120—distal end of needle cover
121—plunger
122—screw thread
123—syringe
124—spring
125—injection site
130—proximal end of body
131—distal end of body
132—inner housing
133—aperture
134—aperture
135—aperture
136—aperture
137—arm
138—arm
139A—arm
139B—arm
140—distal end of needle
144—axis
200—device The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten. An example of an oligonucleotide is, for example: mipomersen sodium (Kynamro®), a capertureserol-reducing antisense therapeutic for the treatment of familial hyper-capertureserolemia or RG012 for the treatment of Alport syndrom. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device.

Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A medicament delivery device comprising:
   a needle for injecting a medicament;
   a body having a proximal end and a distal end;
   a needle cover, wherein the needle cover is axially movable relative to the body from a holding position in which the needle protrudes from the distal end of the needle cover for injecting the medicament, to a locked position in which the needle cover covers a distal end of the needle;
   a biasing member configured to bias the needle cover axially in a distal direction; an inner housing comprising an aperture;
   a collar located at least partially within the inner housing and configured to rotate relative to the inner housing, wherein the collar comprises an arm; and
   a rotational member for rotating the collar from a first position to a second position,
   wherein the needle cover is arranged radially outwardly from the inner housing, and wherein when the needle cover is in the locked position and the collar is in the second position then the arm extends radially through the aperture to a blocking position and contacts a proximal end of the needle cover to block proximal movement of the needle cover away from the locked position.

2. The medicament delivery device according to claim 1, wherein the needle cover at least partially covers the aperture when the needle cover is in the holding position for restricting radial movement of the arm through the aperture.

3. The medicament delivery device according to claim 1, wherein the needle cover is axially movable relative to the body from an initial position, in which the needle cover covers the distal end of the needle, to the holding position.

4. The medicament delivery device according to claim 3, wherein the aperture is a first aperture, and wherein the inner housing comprises a second aperture for receiving the arm.

5. The medicament delivery device according to claim 4, wherein the arm extends through the second aperture when the needle cover is in the initial position and the collar is in the first position.

6. The medicament delivery device according to claim 1, wherein the arm is a first arm, and wherein the collar further comprises a second arm.

7. The medicament delivery device according to claim 6, wherein the inner housing comprises a further aperture for receiving the second arm, and wherein when the needle cover is in the locked position and the collar is in the second position then the second arm extends radially through the further aperture to a second blocking position and blocks proximal movement of the needle cover away from the locked position.

8. The medicament delivery device according to claim 7, wherein the needle cover at least partially covers the further aperture when the needle cover is in the holding position for restricting radial movement of the second arm through the further aperture.

9. The medicament delivery device according to claim 7, wherein the inner housing comprises an additional aperture, and wherein the second arm extends through the additional aperture when the needle cover is in an initial position and the collar is in the first position.

10. The medicament delivery device according to claim 7, wherein the second arm is positioned within the further aperture when the needle cover is in the holding position and the collar is in the second position.

11. The medicament delivery device according to claim 1, wherein the arm is radially biased towards the blocking position.

12. The medicament delivery device according to claim 1, wherein the inner housing supports the rotational member.

13. The medicament delivery device according to claim 1, wherein the rotational member is a spring the rotational member is a torsion spring.

14. The medicament delivery device according to claim 1, wherein rotation of the collar from the first position to the second position causes the medicament to be dispensed from the device via the needle.

15. The medicament delivery device according to claim 1, wherein the medicament delivery device is configured to inject greater than 2 ml of the medicament.

16. The medicament delivery device according to claim 1, wherein the medicament delivery device is configured to inject the medicament having a viscosity of greater than 25 cP.

17. The medicament delivery device according to claim 1, wherein the device comprises the medicament.

18. The medicament delivery device according to claim 1, wherein the arm is positioned within the aperture when the needle cover is in the holding position and the collar is in the second position.

19. The medicament delivery device according to claim 1, wherein the arm is not located in the aperture when the collar is in the first position and the needle cover is in an initial position.

20. The medicament delivery device according to claim 1, wherein the arm is flexible.

21. The medicament delivery device according to claim 1, wherein the device further comprises a spring which biases the arm radially outwards.

22. A method of locking a medicament delivery device after medicament has been dispensed from the medicament delivery device, the method comprising: moving a needle cover of the device to a locked position in which the needle cover covers a distal end of a needle of the device, wherein when the needle cover is in the locked position, proximal movement of the needle cover away from the locked position is blocked by an arm of a collar located at least partially within an inner housing of the medicament delivery device, wherein the collar is configured to rotate relative to the inner housing from a first position to a second position, wherein the arm extends radially through an aperture of the inner housing to a blocking position when the collar is in the second position, and wherein the arm contacts a proximal end of the needle cover to block proximal movement of the needle cover away from the locked position when the arm is in the blocking position.

23. A method of using a medicament delivery device, the method comprising: removing the medicament delivery device from an injection site, wherein removing the medicament delivery device from the injection site moves a needle cover of the device to a locked position in which the needle cover covers a distal end of a needle, wherein when the needle cover is in the locked position, proximal movement of the needle cover away from the locked position is blocked by an arm contacting a proximal end of the needle cover, wherein a collar comprises the arm and is located at least partially within an inner housing of the medicament delivery device, wherein the collar is configured to rotate relative to the inner housing from a first position to a second position, wherein when the collar is in the second position, the arm extends radially through an aperture of the inner housing to a blocking position and contacts the proximal end of the needle cover to block the proximal movement of the needle cover away from the locked position.

24. The method according to claim 23, further comprising the preceding step of pressing the medicament delivery device against the injection site to move the needle cover from an initial position to a holding position for dispensing medicament from the device.

25. The method according claim 24, further comprising holding the medicament delivery device in the holding position whilst the medicament is dispensed from the device.

* * * * *